United States Patent [19]

Newhouse et al.

[11] Patent Number: 5,290,753
[45] Date of Patent: Mar. 1, 1994

[54] METHOD FOR THE PREVENTION OF CROP INJURY IN THE PRESENCE OF SYNERGISTIC PESTICIDE COMBINATIONS

[75] Inventors: Keith E. Newhouse, Bensalem; Thomas J. Schaefer, Levittown, both of Pa.; Gail E. Cary, Lawrenceville, N.J.

[73] Assignee: American Cyanamid Company, Wayne, N.J.

[21] Appl. No.: 881,904

[22] Filed: May 12, 1992

Related U.S. Application Data

[63] Continuation of Ser. No. 521,213, May 9, 1990, abandoned.

[51] Int. Cl.$^5$ .............. A01H 4/00; A01N 43/48; A01N 57/00
[52] U.S. Cl. ................... 504/214; 504/215; 504/247; 504/253; 514/75; 435/172.3; 935/64; 800/DIG. 56
[58] Field of Search .............. 435/240.4, 172.3, 172.1; 800/200, 205, 220, 230; 935/64; 47/57.6; 514/75; 504/214, 215, 247, 253

[56] References Cited

U.S. PATENT DOCUMENTS

| | | |
|---|---|---|
| 3,749,566 | 7/1973 | Hoffmann et al. |
| 4,343,649 | 8/1982 | Sweetser |
| 4,761,373 | 8/1988 | Anderson et al. ............... 435/172.3 |
| 4,992,092 | 2/1991 | Birk et al |

OTHER PUBLICATIONS

Swanson, et al (1988) Plant Cell Reports 7:83–87.
Wiersma, et al. (1989) Mol. Gen. Genet. 219:413–420.
Gough, et al. (1988) Queensland Journal of Agricultural and Animal Sciences 45:9–17.
Finlayson (Apr. 1979) Can. J. Plant Sci 59:399–410.
Fuerst et al. (1986) Weed Science 34:344–353.
Anderson et al. 07/169,094 Mar. 8, 1988.

*Primary Examiner*—Che S. Chereskin
*Attorney, Agent, or Firm*—Michael P. Morris

[57] ABSTRACT

The present invention provides a method for protecting or preventing a crop from injury due to the application of a combination of compounds by altering the susceptibility of the crop by incorporating a gene resistant to inhibition by at least one of the compounds in the combination into the genome of the crop.

10 Claims, No Drawings

METHOD FOR THE PREVENTION OF CROP INJURY IN THE PRESENCE OF SYNERGISTIC PESTICIDE COMBINATIONS

This application is a continuation of copending application Ser. No. 07/521,213, filed May 9, 1990, now abandoned.

BACKGROUND OF THE INVENTION

The interaction of pesticides which when applied in combination, either simultaneously or sequentially, result in responses not predictable from the performance of each pesticide applied singly is of major concern to agriculturalists. Of particular concern are synergistic responses which occur on a single plant species. Synergistic responses obtained with combinations of herbicides, insecticides and fungicides are described as the combined action of two components of a mixture such that the total effect is greater or more prolonged than the sum of the effects of the two components taken independently.

Simultaneous or sequential applications of herbicides, fungicides and insecticides are common in the production of many food and fiber crops; however, synergistic pesticide combinations may cause problems in crop production due to increased toxicity to crop plants and other nontarget species and increased residue burdens in crops or soil.

Methods directed towards protecting a crop from inhibition of growth and development due to a single pesticidal compound, such as an herbicide, are found in U.S. Pat. Nos. 4,343,649 and 3,749,566 and in copending patent applications Ser. Nos. 292,207 filed Dec. 30, 1988 and 169,094 filed Mar. 8, 1988. However, no methods directed towards protecting or preventing a crop from injury due to a combination of pesticidal compounds have been described.

It is, therefore, an object of this invention to provide a method for protecting or preventing a crop from injury due to the application of a combination of pesticidal compounds by altering the susceptibility of the crop to one or more components of the combination by incorporating a pesticide resistance gene into the genome of the crop.

SUMMARY OF THE INVENTION

A combination of several herbicides, insecticides, nematicides and fungicides may be applied to a crop in a single growing season. In many instances, two or more pesticides applied at the same time act wholly independently. However, there are many known instances of considerable modifications in the biological activity of one pesticide brought about by the prior, simultaneous or sequential application of another pesticide to the same target species. When this occurs it is commonly referred to as an "interaction". As a result of pesticide interactions, adverse effects can occur and the responses of target species such as crop plants to combined applications of two or more pesticides are not predictable from the effect of each pesticide applied alone. Said interactions are described as antagonistic when the net effect is a decrease in the biological activity and synergistic when the net effect is an enhancement of biological activity. In other words, a synergistic interaction of a pesticide combination is a substantially more than additive toxic action of two or more pesticides when used together. Pesticide combination applications which result in a synertistic interaction are herein described as synergistic pesticide combinations.

It has now been found that the incorporation of a resistance gene into the target species such as a crop plant imparts enhanced tolerance or resistance of said species to the pesticidal compounds applied in combination. Well characterized single genes with a clearly discernible level of resistance may be incorporated into the crop plant by the mutational alteration of resident genes via plant breeding techniques, tissue culture selection or genetic transformation. Such pesticide resistance genes include genes encoding altered forms of the enzyme (or protein) which normally inhibits the activity of the pesticide as well as genes encoding enzymes capable of metabolizing said pesticide.

Injury to a crop due to the application of a combination of compounds is prevented or substantially reduced by altering the susceptibility of said crop to one or more of the applied compounds. The susceptibility of the crop may be altered by the incorporation of a pesticide resistance gene by mutational alteration of resident genes via tissue culture selection, plant breeding techniques or genetic transformation.

DETAILED DESCRIPTION OF THE INVENTION

In one embodiment of the method of the invention, the prevention of injury to a crop such as maize, rice, wheat, millet, rape seed, grain sorghum, sugarbeets, soybeans, cotton, potatoes, tomatoes or peanuts due to the sequential application of an organophosphate soil insecticide and an acetohydroxyacid synthase (AHAS) enzyme inhibiting herbicide is accomplished by the incorporation of an herbicide insensitive AHAS enzyme into the crop species.

In agronomic practice, soil insecticides are commonly used to provide immediate control of pests present in the soil and systemic control of pests which attach crop roots or shoots. These soil insecticides may be applied prior to, concurrently with or subsequent to the planting of said crop. The application of the insecticide may be made directly in the seed furrow or into a band of soil around the planted seed that may, or may not, include the actual zone into which the seed is planted. Among the soil insecticides suitable for the present invention are organophosphate insecticides such as terbufos, phorate, parathion, fonofos, disulfoton and chlorpyrifos. Insecticide application may then be followed by the application of an AHAS inhibiting herbicide such as an imidazolinyl nicotinate, an imidazolinyl quinolinecarboxylate, a sulfonylurea or a triazolopyrimidine either preemergence or postemergence. Alternatively, the AHAS inhibiting herbicide may be applied to the soil prior to planting, incorporated into the soil and the soil insecticide applied just prior to, concurrently with or just after planting. Among the AHAS inhibiting herbicides that may be used in the present invention are imazethapyr, imazmethapyr, imazaquin, imazmethabenz, primisulfuron and nicosulfuron.

The susceptibility of a plant species to the synergistic interaction resulting from the application of a combination of pesticides wherein one of the pesticide components is an AHAS inhibiting herbicide is altered by the incorporation of a resistance gene encoding an herbicide insensitive AHAS enzyme. Said resistance gene may be incorporated from related species by conventional genetic crosses, selected by tissue culture, developed by mutation breeding techniques or incorporated by gene transfer methods including, but not limited to, genetic engineering and plant transformation techniques. A method for the production of plants, plant tissue and plant seed which contain an herbicide resistant AHAS enzyme is described in U.S. Pat. No. 4,761,373, which is incorporated herein by reference thereto. Plants, plant tissue and plant seed bred to include a gene encoding an herbicide insensitive AHAS enzyme demonstrate resistance to growth inhibition due to a synergistic interaction of a pesticide combination wherein one of the components is an AHAS inhibiting pesticide at combination application rates which normally inhibit the growth and development of said plants, plant tissue and plant seed not possessing a gene encoding an herbicide resistant AHAS enzyme.

In a particular embodiment of the invention, plant tissue cultures which demonstrate resistance to an AHAS inhibiting herbicide are selected and plants which are resistant to said herbicide are regenerated from these cultures. These plants are cross pollinated with plants of an herbicide sensitive inbred line. Seeds obtained from the mature plants resulting from these crossings are planted, grown to sexual maturity and self-pollinated. The selfing process is repeated for a second generation. Seed is harvested from individual plants and kept separated. Homozygous resistant progeny may be identified from these plants by using a seedling assay for herbicide resistance.

The herbicide resistance gene may be incorporated by standard breeding methods such as backcrossing to create commercial cultivars homozygous for the resistance trait. In the case wherein the plant is corn, these cultivars are inbred lines uniformly homozygous for the resistance trait. Crosses between inbred lines uniformly homozygous for the resistance trait may be made to produce hybrid seed uniformly homozygous for the resistance gene. Alternatively, these homozygous resistant inbred lines may be used, as either a male or female parent, in crosses with plants lacking the resistance gene to produce hybrid seed which is uniformly heterozygous for the resistance gene.

In order to facilitate a further understanding of the invention, the following examples are presented primarily for the purpose of illustrating more specific details thereof. The invention is not to be deemed limited thereby except as defined in the claims. Unless otherwise noted, all parts are by weight.

EXAMPLE 1

Evaluation Of The Effect Of The Interaction Of A Pesticide Combination On Corn Plants Which Have Altered Suceptibility Due To The Introduction Of A Pesticide Resistance Gene The corn seeds used in this experiment are a heterozygous resistant hybrid (B73xM017) containing a single copy of a resistance gene, either XA-17 or XI-12, (designated as XA17HE and XI12HE, respectively) a homozygous resistant hybrid (B73xM017) containing 2 copies of a resistance gene, XA-17, designated as XA17HO and a susceptible hybrid (B73xM017) containing no resistance genes.

The pesticide combination applied in this experiment is an organophosphate soil insecticide and an AHAS inhibiting herbicide. The soil insecticide is terbufos present as a commercial granular formulation containing 15% wt/wt of active ingredient (COUNTER ® 15G) and the AHAS inhibiting herbicide is imazethapyr present as a commercial aqueous solution formulation containing 24% wt/wt of active ingredient (PURSUIT ® 2AS).

Standard 25×50 cm flats filled with Sassafrass sandy loam soil are lightly watered and left to drain for about 2 hours. Into the moistened soil are cut 3 equally spaced furrows, each about 2.5 cm in width, 15.2 cm in length and about 1.2 to 2.5 cm in depth. Five corn seeds are placed in each furrow, the soil insecticide is added over the seed at rates corresponding to about 1.0 to 2.0 kg/ha of active compound and the furrows are closed by hand. The flats are then sprayed with an aqueous solution containing the herbicide in sufficient quantity to provide the equivalent of about 0.07 to 0.21 kg/ha of active compound when operating a spray nozzle at 40 psi for a predetermined time. After spraying, the flats are placed on greenhouse benches and are cared for in the manner commensurate with conventional greenhouse practices. At 3 weeks after treatment the seedling plants are examined and plant heights are measured and recorded. The mean plant heights are calculated and shown in Table I.

TABLE I

Evaluation Of The Effect Of The Combination Of A Soil Insecticide Applied In-Furrow And An Herbicide Applied Preemergence On Corn Plants Having Altered Susceptibility

| Genotype (B73xMO17) | Herbicide kg/ha | Mean Plant Heights (cm) Insecticide | | |
| --- | --- | --- | --- | --- |
| | | 0.0 kg/ha | 1.0 kg/ha | 2.0 kg/ha |
| XA17HE | 0.00 | 55 | 51 | 53 |
| XA17HE | 0.07 | 46 | 33 | 42 |
| XA17HE | 0.14 | 33 | 28 | 32 |
| XA17HE | 0.21 | 35 | 38 | 28 |
| XI12HE | 0.00 | 52 | 57 | 50 |
| XI12HE | 0.07 | 53 | 51 | 56 |
| XI12HE | 0.14 | 52 | 51 | 49 |
| XI12HE | 0.21 | 57 | 41 | 42 |
| XA17HO | 0.00 | 49 | 55 | 55 |
| XA17HO | 0.07 | 63 | 58 | 63 |
| XA17HO | 0.14 | 62 | 51 | 58 |
| XA17HO | 0.21 | 66 | 49 | 52 |
| Susceptible | 0.00 | 42 | 45 | 54 |
| Susceptible | 0.07 | 0 | 0 | 0 |
| Susceptible | 0.14 | 0 | 0 | 0 |
| Susceptible | 0.21 | 0 | 0 | 0 |

EXAMPLE 2

Evaluation Of The Effect Of The Interaction Of A Pesticide Combination On Corn Plants Possessing A Pesticide Resistance Gene The corn seed used in this experiment are a heterozygous resistant hybrid (B73xM017) containing a single copy of a resistance gene, either XA-17 or XI-12, designated as XA17HE and XI12HE respectively, a homozygous resistant hybrid (B73xM017) containing two copies of a resistance gene, XA-17, designated as XA17HO and a susceptible hybrid (B73xM017) containing no resistance genes.

The pesticide combination applied in this experiment is an organophosphate soil insecticide and an AHAS inhibiting herbicide. The soil insecticide is terbufos present as a commercial granular formulation containing 15% wt/wt of active ingredient (COUNTER ® 15 G) and the AHAS inhibiting herbicide is imazethapyr present as a commercial aqueous solution formulation containing about 21.6% wt/wt of active ingredient (PURSUIT ® 2AS).

Standard 25×50 cm flats filled with a greenhouse soil mix are lightly watered and left to drain for about 2 hours. Greenhouse soil mix is an artificial soil mix consisting of Sassafras sandy loam, muck and sand as a 1:1:2, v/v/v, mixture. Into the drained soil are cut 3 equally spaced furrows each about 2.5 cm in width, 15.2 cm in length and about 1.2 to 2.5 cm in depth. Five corn seeds are placed in each furrow, the soil insecticide is added over the seed at rates corresponding to about 1.0 to 2.0 kg/ha of active compound and the furrows are closed by hand. The plants are allowed to grow to about the 2 to 3 leaf stage and are then sprayed with an aqueous solution containing 0.25% v/v of TWEEN® 20, a polyoxyethylene sorbitan monolaurate surfactant manufactured by Atlas Chemical Industries and the herbicide in sufficient quantity to provide about 0.07 to 0.21 kg/ha of active compound when operating a spray nozzle at 40 psi for a predetermined time. After spraying, the plants are placed on greenhouse benches and cared for in the usual manner. One week after treatment the plant heights are measured and recorded. The mean plant heights are calculated and reported in Table II.

TABLE II

Evaluation Of The Effect Of The Interaction Of A Soil Insecticide Applied In-Furrow And An Herbicide Applied Postemergence On Corn Plants Possessing A Resistance Gene

| Genotype (B73xMO17) | Herbicide kg/ha | Mean Plant Heights (cm) Insecticide | | |
|---|---|---|---|---|
| | | 0.0 kg/ha | 1.0 kg/ha | 2.0 kg/ha |
| XA17HE | 0.00 | 41 | 40 | 39 |
| XA17HE | 0.07 | 31 | 21 | 20 |
| XA17HE | 0.14 | 26 | 20 | 22 |
| XA17HE | 0.21 | 22 | 20 | 21 |
| XI12HE | 0.00 | 34 | 38 | 38 |
| XI12HE | 0.07 | 36 | 23 | 20 |
| XI12HE | 0.14 | 39 | 25 | 26 |
| XI12HE | 0.21 | 36 | 24 | 24 |
| XA17HO | 0.00 | 31 | 34 | 32 |
| XA17HO | 0.07 | 35 | 31 | 32 |
| XA17HO | 0.14 | 31 | 32 | 30 |
| XA17HO | 0.21 | 34 | 35 | 32 |
| Susceptible | 0.00 | 32 | 37 | 38 |
| Susceptible | 0.07 | 0 | 0 | 0 |
| Susceptible | 0.14 | 0 | 0 | 0 |
| Susceptible | 0.21 | 0 | 0 | 0 |

EXAMPLE 3

Evaluation Of The Effects Of The In-Furrow Application Of A Soil Insecticide Combined With The Postemergence Application Of An Herbicide On Corn Plants Possessing A Pesticide Resistance Gene Standard 5 inch pots filled with a greenhouse soil mix are sown with the corn seeds which are described hereinabove in Examples 1 and 2 at the rate of one seed per pot. A soil insecticide, (terbufos) is applied in-furrow at a rate of 1.0 kg/ha to one-half of the pots. The plants are grown to about the 2 to 3 leaf stage and are then sprayed with a herbicide (imazethapyr) at rates of about 0.035 to 0.84 kg/ha. The plants are placed on greenhouse benches and cared for in the usual manner. At 0, 7, 14 and 28 days after treatment (DAT) plant heights are measured and recorded. The % growth is calculated as shown below.

$$\frac{\text{height at } DAT \text{ minus height at day 0}}{\text{control height at } DAT \text{ minus control height at day 0}} \times 100 = \% \text{ Growth}$$

The data obtained are shown in Table III.

TABLE III

Evaluation Of The Effects Of The Interaction Of A Pesticide Combination On Susceptible Plants And Plants Having An Altered Susceptibility

| Genotype (B73xM017) | Herbicide kg/ha | % Growth | | | | | |
|---|---|---|---|---|---|---|---|
| | | 7 DAT | | 14 DAT | | 28 DAT | |
| | | Insecticide | | | | | |
| | | 0.0 kg/ha | 1.0 kg/ha | 0.0 kg/ha | 1.0 kg/ha | 0.0 kg/ha | 1.0 kg/ha |
| XA17HE | 0.0 | 100.0 | 100.0 | 100.0 | 99.4 | 100.0 | 104.0 |
| XA17HE | 0.035 | 75.5 | 37.8 | 90.1 | 67.9 | 100.4 | 104.6 |
| XA17HE | 0.07 | 64.2 | 28.6 | 72.2 | 59.3 | 98.8 | 97.5 |
| XA17HE | 0.14 | 30.4 | 26.6 | 57.4 | 31.5 | 88.8 | 86.3 |
| XA17HE | 0.21 | 27.6 | 21.4 | 44.4 | 16.1 | 81.3 | 54.2 |
| XA17HE | 0.42 | 22.4 | 20.4 | 29.0 | 13.6 | 77.9 | 63.3 |
| XI12HE | 0.0 | 100.0 | 95.2 | 100.0 | 100.0 | 100.0 | 105.5 |
| XI12HE | 0.035 | 92.4 | 81.0 | 96.3 | 93.2 | 106.0 | 105.5 |
| XI12HE | 0.07 | 92.4 | 78.1 | 92.6 | 90.7 | 104.0 | 104.2 |
| XI12HE | 0.14 | 88.6 | 77.1 | 89.5 | 87.0 | 100.8 | 102.1 |
| XI12HE | 0.21 | 87.6 | 25.7 | 92.0 | 60.5 | 96.6 | 100.9 |
| XI12HE | 0.42 | 53.1 | 33.3 | 78.0 | 50.6 | 100.4 | 94.9 |
| XA17HO | 0.0 | 100.0 | 86.5 | 100.0 | 107.2 | 100.0 | 102.4 |
| XA17HO | 0.07 | 92.1 | 88.8 | 105.6 | 105.6 | 102.4 | 108.2 |
| XA17H0 | 0.14 | 91.0 | 85.4 | 98.4 | 109.6 | 109.2 | 107.7 |
| XA17H0 | 0.21 | 85.4 | 79.8 | 108.0 | 99.2 | 113.0 | 110.1 |
| XA17H0 | 0.42 | 83.1 | 84.3 | 99.2 | 106.4 | 111.6 | 114.5 |
| XA17H0 | 0.84 | 91.0 | 82.0 | 106.4 | 103.2 | 115.0 | 110.1 |
| Susceptible | 0.0 | 100.1 | 100.1 | 100.0 | 97.5 | 100.0 | 96.9 |
| Susceptible | 0.035 | 31.3 | 7.3 | 59.9 | 4.5 | 95.0 | 20.1 |
| Susceptible | 0.07 | 20.4 | 9.4 | 27.4 | 3.8 | 61.1 | 16.2 |

What is claimed is:

1. A method for protecting a maize plant from injury or preventing injury of a maize plant due to the application of a combination of compounds consisting of an acetohydroxy acid synthase inhibiting herbicide and an organophosphate insecticide which comprises altering the susceptibility of the maize plant to the combination by incorporating a resistance gene encoding an altered acetohydroxy acid synthase into the genome of the maize plant and applying to the maize plant a combination of an acetohydroxy acid synthase inhibiting herbicide and an organophosphate insecticide.

2. The method according to claim 1, wherein the gene is selected from the group consisting of XA-17, XI-12, QJ-22, XS-40 ZA-54.

3. The method according to claim 2, wherein the gene is XA-17 or XI-12 which is present in the homozygous state.

4. The method according to claim 2, wherein the gene is XA-17 or XI-12 which is present in the heterozygous state.

5. The method according to claim 1, wherein the insecticide is selected from the group consisting of terbufos, phorate, parathion, fonofos, disulfoton and chlorpyrifos.

6. The method according to claim 1, wherein the herbicide is selected from the group consisting of imidazolinyl nicotinates, imidazolinyl quinolinecarboxylates, sulfonylureas and triazolopyrimidines.

7. The method according to claim 1, wherein the insecticide is terbufos and the herbicide is selected from the group consisting of imazethapyr, imazmethapyr, imazaquin, primisulfuron and nicosulfuron.

8. The method according to claim 5, wherein the herbicide is imazethapyr.

9. The method according to claim 5, wherein the herbicide is primisulfuron.

10. The method according to claim 5, wherein the herbicide is nicosulfuron.

* * * * *